(12) United States Patent
Cui et al.

(10) Patent No.: US 6,878,731 B2
(45) Date of Patent: Apr. 12, 2005

(54) **IMIDAZOLE ALKALOIDS FROM *LEPIDIUM MEYENII* AND METHODS OF USAGE**

(75) Inventors: Baoliang Cui, Palisade Park, NJ (US); Bo Lin Zheng, Aurora, CO (US); Kan He, River Edge, NJ (US); Qun Yi Zheng, Wayne, NJ (US)

(73) Assignee: Pure World Botanicals, Inc., South Hackensack, NJ (US)

( * ) Notice: Subject to any disclaimer, the term of this patent is extended or adjusted under 35 U.S.C. 154(b) by 0 days.

(21) Appl. No.: 10/219,056

(22) Filed: Aug. 14, 2002

(65) Prior Publication Data

US 2004/0034079 A1 Feb. 19, 2004

(51) Int. Cl.[7] ............................................. A61K 31/415

(52) U.S. Cl. ....................................... 514/385; 514/396

(58) Field of Search .......................... 514/385, 396–400

(56) References Cited

U.S. PATENT DOCUMENTS

| 4,481,211 A | * | 11/1984 | Dockner et al. | ............. | 514/396 |
| 4,605,661 A | * | 8/1986 | Hirsch et al. | ................ | 514/400 |
| 4,916,144 A | * | 4/1990 | Strehlke et al. | ............. | 514/326 |

OTHER PUBLICATIONS

Internal Medicine, 4th Edition, Editor–in–Chief Jay Stein, Chapters 71–72, pp. 699–715.*

* cited by examiner

*Primary Examiner*—Dwayne Jones
(74) *Attorney, Agent, or Firm*—Steven C. Petersen; Townsend and Townsend and Crew LLP

(57) ABSTRACT

The present invention relates to novel imidazole alkaloid compounds that have been isolated as a form of chloride salt from a root extract of *Lepidium meyenii* Walp, with the common name Maca, and identified below as 1,3-bis (phenylmethyl)-4,5-dimethyl-1H-imidazlium chloride and 1,3-bis(phenylmethyl)-2,4,5-trimethyl-1H-imidazlium chloride, compounds (1) and (2), respectively.

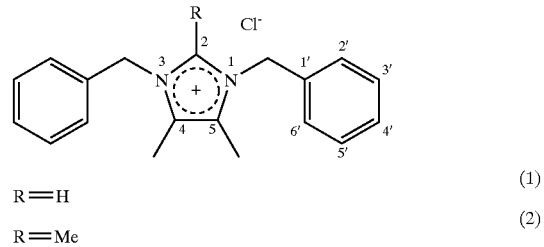

R=H (1)
R=Me (2)

The present invention further relates to the use of these novel compounds (1) and (2) to treat proliferative diseases, such as but not limited to cancer.

2 Claims, 1 Drawing Sheet

IMIDAZOLE ALKALOIDS FROM *LEPIDIUM MEYENII* AND METHODS OF USAGE

BACKGROUND OF THE INVENTION

1. Field of the Invention

The present invention relates to novel imidazole alkaloid compounds that have been isolated as a form of chloride salt from a root extract of *Lepidium meyenii* Walp, with the common name Maca, and identified as 1,3-bis (phenylmethyl)-4,5-dimethyl-1H-imidazlium chloride and 1,3-bis(phenylmethyl)-2,4,5-trimethyl-1H-imidazlium chloride. More specifically, this invention further relates to the use of these novel compounds to treat proliferative diseases, such as but not limited to cancer.

2. Description of the State of Art

*Lepidium meyenii* (commonly referred to as Maca) is indigenous to the Andean Mountains at an altitude of higher than 10,000 feet. To the Andean Indians, Maca is a valuable commodity. Because so little else grows in the region, Maca is often traded with communities at lower elevations for other staples like rice, corn, and beans. The dried roots can be stored for up to seven years. Native Peruvians have traditionally utilized Maca since before the time of the Incas for both nutritional and medicinal purposes. Maca is an important staple in the diets of the people indigenous to the region since it has the highest nutritional value of any food crop grown there. The nutritional value of dried Maca root is high, resembling cereal grains such as maize, rice and wheat. It has 59% carbohydrates, 10.2% protein, 8.5% fiber and 2.2% lipids. It has a large amount of essential amino acids and higher levels of iron and calcium than potatoes. Maca contains important amounts of fatty acids including linolenic, palmitic and oleic acids. It is rich in sterols and has a high mineral content as well. In addition to its rich supply of essential nutrients, Maca contains alkaloids, tannins and saponins. It is rich in sugars, protein, starches, and essential minerals, especially iodine and iron. The tuber is consumed fresh or dried. The fresh roots are considered a treat and are baked or roasted in ashes much like sweet potatoes. The dried roots are stored and later boiled in water or milk to make a porridge. In addition, they are often made into a popular sweet, fragrant, fermented drink called maca chicha.

Maca has been used medicinally for centuries to enhance fertility in humans and animals. Soon after the Spanish conquest in South America, the Spanish found that their livestock were reproducing poorly in the highlands. The local Indians recommended feeding the animals Maca and so remarkable were the results that Spanish chroniclers gave in-depth reports. Even colonial records of some 200 years ago indicate that payments of roughly 9 tons of Maca were demanded from one Andean area alone for this purpose. Its fertility enhancing properties were supported clinically as early as 1961, when researchers discovered it increased the fertility of rats.

Maca is growing in world popularity due to its energizing effects, fertility enhancement and aphrodisiac qualities. Other traditional uses include increasing energy, stamina and endurance in athletes, promoting mental clarity, treating male impotence, and helping with menstrual irregularities and female hormonal imbalances including menopause and chronic fatigue syndrome. It is used as an alternative to anabolic steroids by bodybuilders due to its richness in sterols. Today, dried Maca roots are ground to powder and sold in drug stores in capsules as a medicine and food supplement to increase stamina and fertility. In Peruvian herbal medicine, Maca is also used as an immunostimulant, for anemia, tuberculosis, menstrual disorders, menopause symptoms, stomach cancer, sterility and other reproductive and sexual disorders as well as to enhance memory.

The cultivation of Maca is increasing in the highlands of the Andes to meet the growing demand world wide for medicinal uses. In this severely economically depressed region, the market created for Maca will offer new and important sources of income for the Indigenous Peoples of the Andes. A new cultivar of Maca has been identified in the major growing regions of the highlands, which will supply much of this new demand, and it has been named *Lepidium peruvianum Chacon* sp.

Aguila Calderon, M.D., the former dean of the Faculty of Human Medicine at the National University of Federico Villarreal in Lima uses maca for male impotence, erectile dysfunction, menopausal symptoms and general fatigue, and claims good results. Arizona physician Gary F. Gordon, M.D., former president of the American College for Advancement in Medicine, is also a maca supporter. He calls it "nature's Viagra". The supposed mechanism of action is by normalizing steroid hormones such as testosterone, progesterone and estrogen. It acts on men to restore them to a healthy functional status in which they experience a more active libido. Maca may boost desire but does not share Viagra's erection-enhancing properties.

Scientist Gustavo Gonzales of Peru's Cayetano Heredia University, who led what the scientists say is the world's first study into maca's effect on humans, told a news conference the three-month trial involving 12 volunteer men pointed to an 180–200% lift in libido and up to a doubling of sperm production. Maca produced an increase in sex drive within two weeks. The study, funded by Peruvian pharmaceuticals company Hersil, also found maca reduced blood pressure and had no adverse effect on the heart. Although it also appeared to boost the production and movement of sperm, Gonzales said more research was needed as the test had been restricted to a very small sample.

To be consistent with Peruvian usage levels one should take 3,000–5,000 mg per day of maca, but one can certainly take more. The more maca or maca extract that is consumed, the more the likely benefit. Toxicity studies conducted on maca in the U.S. showed absolutely no toxicity or adverse pharmacological effects. In animal studies, the more maca animals consume, the stronger and more sexually active they become.

In 1981, Johns reported the presence of benzyl isothiocyanates and p-methoxybenzyl isothiocyanate in the roots, which have reputed aphrodisiac properties. Johns, T., *J. Ethnobiol.*, 1:208–212 (1981). Dini, A., et al., also identified many fatty acids, amino acids, and sterols from the roots and tubers in 1994. Dini, A., et al., *O. Food Chem. Toxicol.*, 49:347–349 (1994). A previous in vivo study on lipidic extracts conducted at PureWorld showed the enhancement of sexual function of the mice and rats. Zheng, B. L., et al., *Urology*, 55:598–602 (2000). Two classes of compounds, macaene and macamide, have been identified from the purified standardized products (MacaPure-01 and MacaPure-02), as well as minor constituents of sterols and isothiocyanates. Zheng, B. L., et al., *Urology*, 55:598–602 (2000); and Zheng, B. L., et al., Patent (pending), 1999.

There is still a need, therefore, for a process and procedure for isolating and purifying imidazole alkaloids from imidazole alkaloids containing biomass in a commercially viable manner that directly provides a high concentration of the various imidazole alkaloids that can be subsequently recovered in high yield and purity. There is a further need to determine whether any of the naturally occurring compounds have other beneficial therapeutic uses.

SUMMARY OF THE INVENTION

The present invention relates to novel imidazole alkaloid compounds that have been isolated as a form of chloride salt from a root extract of *Lepidium meyenii* Walp, with the common name Maca, and identified below as 1,3-bis(phenylmethyl)-4,5-dimethyl-1H-imidazlium chloride and 1,3-bis(phenylmethyl)-2,4,5-trimethyl-1H-imidazlium chloride, compounds (1) and (2), respectively.

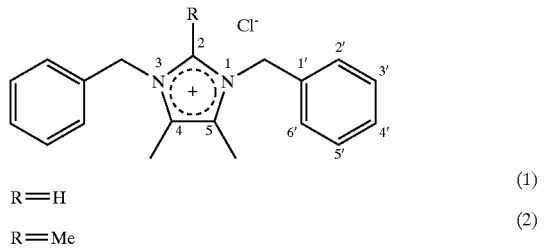

R=H (1)

R=Me (2)

The present invention further relates to the use of these novel compounds (1) and (2) to treat proliferative diseases, such as but not limited to cancer.

Additional objects, advantages, and novel features of this invention shall be set forth in part in the description and examples that follow, and in part will become apparent to those skilled in the art upon examination of the following specification or may be learned by the practice of the invention. The objects and advantages of the invention may be realized and attained by means of instrumentalities, combinations, compositions, and methods particularly pointed out in the appended claims.

BRIEF DESCRIPTION OF THE DRAWINGS

The accompanying drawings, which are incorporated in and form a part of the specifications, illustrate the preferred embodiments of the present invention, and together with the description serve to explain the principles of the invention. In the Drawing.

DETAILED DESCRIPTION OF THE PREFERRED EMBODIMENT

Figure 1:
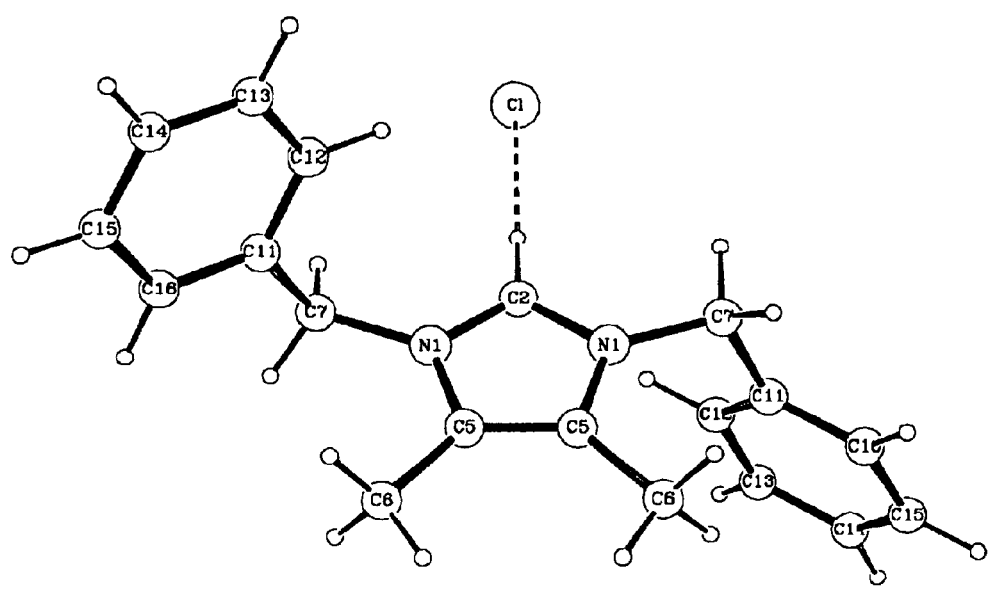
FIG. 1 is a perspective view of the molecular structure of the compound (1) as determined by X-ray crystallography.

In general the present invention relates to novel imidazole alkaloid compounds identified as 1,3-bis(phenylmethyl)-4,5-dimethyl-1H-imidazlium chloride (1)

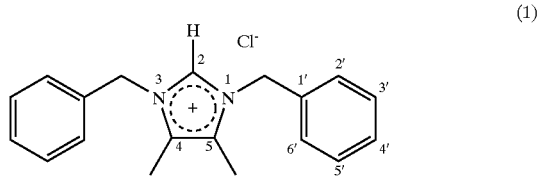

(1)

and 1,3-bis(phenylmethyl)-2,4,5-trimethyl-1H-imidazlium chloride (2)

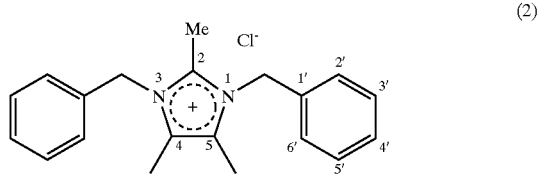

(2)

and methods of use to treat proliferative diseases such as cancer. While compound (1) and compound (2) were isolated form *L. meyenii* as described in further detail below one skilled in the art of chemical synthesis would be able to compounds (1) and (2) and analogs such as compound (3)

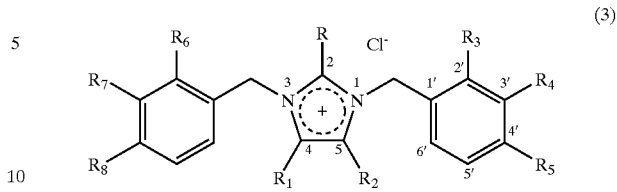

(3)

wherein, R, $R_1$, $R_2$, $R_3$, $R_4$, $R_5$, $R_6$, $R_7$, and $R_8$ are hydrogen, hydroxyl, methyl, methoxyl, aldehyde, COOH, Cl, I, F, S, P, $NO_3$, $NO_2$, $NH_2$ groups, or combinations thereof. Consequently, compounds (1), (2) and (3) of the present invention are not to be construed as limited to being originated from a particular biomass.

The present invention may be achieved by a unique extraction and isolation process. Roots of *L. meyenii* having been cleaned with water are mixed or contacted with a first solvent, such as but not limited to ethanol, with a plant material containing compounds (1) and (2). Other organic solvents that may be used for the extraction step are water, methanol, acetone, ethyl acetate, chloroform, and dichloromethane. Depending on the type of plant material used or its physical condition, it may be necessary to grind it into a range 0.1–10 min. The degree of comminutation of the plant material should provide sufficient particulate surface area for the first solvent to contact, but again this depends on the type of plant material used. The skilled person in this art will recognize that a variety of extraction methods are available in the literature, such as, percolation, vat extraction, countercurrent extraction, etc. The particular method of extraction employed is not essential to the process of the present invention. In the extraction process, the temperature of extraction is between 40°–70° C., with 50°–60° C. being preferred. The amount of plant material to solvent mixture used in the extraction process varies between 1:1 to 1:10 on a gram:millimeter basis, with 1:3 to 1:7 being preferred. The imidazole alkaloid compounds (1) and (2) and some of the extraneous materials that are contained in the comminuted plant material are soluble in the first solvent used. Thus, the first solvent, compounds (1) and (2) and some of the extraneous materials form the crude extract. The crude extract is next dissolved with a second organic solvent such as but limited to methanol to a final volume of 20% solid in w/w at a temperature in the range of 40° C. to 60° C. and preferably 50° C. An acid such as but not limited to hydrogen chloride is slowly stirred in and allowed and this mixture is allowed to stand for a period of time sufficient to achieve a precipitate and an aqueous phase. The precipitate is seperated from the acidic water-methonal solvent and extracted at least two more times as described above.

The resulting aqueous phase is then extracted multiple times using methylene chloride and the methylene chloride layers are combined and evaporated to dryness to afford a first extract. The remaining aqueous phase is centralized and adjusted to a pH of about 12 with 5N sodium hydroxide, and then extracted with methylene chloride to afford a second extract.

After completion of the formation of the first extract, the second step, the separation of compounds (1) and (2), begins. Since the first extract contains not only the desired compounds (1) and (2) but also extraneous materials that are soluble in the first solvent of the crude extract, it is desirable to recover the compounds (1) and (2) with as little extraneous material as possible. The following step, of the isolation of the compounds (1) and (2) from the first extract, includes the partial elimination of unwanted extraneous materials such as phenols, H$_2$O, proteins, simple and complex sugars, etc., while selectively maintaining compounds (1) and (2). To recover compounds (1) and (2) the first extract is loaded onto a column such as but not limited to reversed phase. In this step the preferred adsorbent is Diaion HP20. Subsequent to adsorbing the compounds (1) and (2) to matrix and eluted in fractions using a series of specific solvents each having a volume five times that of the column that supports the matrix and comprising a specific ratio of a second solvent, such as an alcohol to water in combination with acetic acid and acetone. The preferred alcohol is methanol or ethanol. Molecules having the lowest affinity for the adsorbent are specifically desorbed passing directly through the matrix and collected in the first wash column volume. With each successive column volume of eluting solvent the specific ratio of the second solvent to water increases and the compounds (1) and (2) are specifically desorbed in sequence according to their affinity for the adsorbent.

The collected fractions are subjected to thin layer chromatography in a solvent system and the plate is dipped into Dragendorff's reagent to reveal the alkaloid-positive spots are contained in the second fraction. The second fraction is subfractionated over normal phase silica gel column chromatography to give seven fractions. Fraction five was collected and fractionated over an acid type column to yield a crude alkaloid fraction which was further purified by a combination of column chromatography and preparative HPLC on silica gel to yield compound (1) and (2).

The preferred third and final step in the process is the crystallization or final purification of each compound (1) and (2). To begin, compounds (1) and (2) from the preceding step are dissolved (5 mg/ml) in a volume of solvent, respectively, the preferred solvent is acetone/methanol, however acetone/ethanol will also suffice. The resulting suspension is then crystallized by refrigerating the solution overnight. The refrigerated suspension is then passed through a filter ant the final product, the crystallized compounds (1) and (2), are collected and dried. Both compounds (1) and (2) crystallized well to afford white needles in acetone and white plates in 10% acetone/methanol.

The following non-limited example provides a specific high yield process for isolating compounds (1) and (2). All scientific and technical terms have the meanings as understood by one with ordinary skill in the art. The descriptions and specific examples that follow are only intended for the purposes of illustration, and are not to be construed as limiting in any manner to isolated the compounds of the present invention by other methods. As discussed synthetic routes to achieve the compounds of the present invention are embraced by this invention but not specifically disclosed. Further, variations of the methods to produce the same compounds in somewhat different fashion will be evident to one skilled in the art.

All temperatures are understood to be in Centigrade (° C.) when not specified. The nuclear magnetic resonance (NMR) spectral characteristics refer to chemical shifts δ expressed in parts per million (ppm) versus tetramethylsilane (TMS) as reference standard. $^1$H and $^{13}$C NMR spectra were recorded on Varian XL-400 instrument with tetramethylsilane (TMS) as internal standard. Low-resolution ESIMS spectra were measured with a Finnigan MAT-LCQ instrument. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiple (m), doublet (d), quartet (q), triplet (t), doublet of doublet (dd), doublet of triplet (dt), and doublet of quartet (dq). The solvents employed for taking NMR spectra are DMSO-d$_6$ (perdeuterodimethysulfoxide), D$_2$O deuterated water), CDCl$_3$ (deuterochloroform) and other conventional deuterated solvents. The chemical shifts are expressed in ppm relative to the reference of CDCl$_3$ or DMSO. Deuterated solvents were purchased from Aldrich Chemical Co. The IR spectra were recorded on a Midac Collegian FT-IR interferometer. The X-ray data were measured on an Enral-Nonius CAD4 diffractometer (graphite-monochromated Mo Kα radiation, ω-2 θ scans). TLC plates of silica gel 60F254 were purchased from E. M. Merck and kept in a closed container over Drierite® prior to use. Melting points were measured on a MEL-TEMP II apparatus equipped with a digital Barnant 100 Thermocouple Thermometer and are uncorrected. HPLC was performed on a Hitachi chromatographic spectrometer (L-6200A Intelligent Pump, D-6000 Interface, L-4000 UV Detector and AS-4000 Intelligent Auto Sampler). Combination of CH$_3$CN and H$_2$O in different concentrations are used as HPLC solvent system. All solvents were distilled before use. Commercially available chemicals were used without any further purification. Various methods of purifying the products of the present invention are known and understood by those skilled in the art and the purification methods presented in the Examples is solely listed by way of example and is not intended to limit the invention.

EXAMPLE I

Experimental Section

Plant Material. The roots of *L. meyenii* (Solanaceae) were collected in Andean Mountains, Peru in 1998. A Voucher specimen representing this collection has been deposited at the Herbrio de Museo de Historia Natural 'J. Prado" Un. H. S., Lima, Peru.

Extraction and Isolation. The air-dried roots (10 kg) of *L. meyenii* were washed with water, and then extracted with three changes of 100% SDA. After removal of organic solvent, the resultant extracts (2 kg) was dissolved in 10 L of MeOH with heat at 50° C., followed by adding 7 L of 1N hydrogen chloride (HCl) solution slowly with stirring and allowed to stand for 4 hours. The acidic H$_2$O—MeOH solvent was seperated from the precipate that was treated the same way twice. After removal of organic solvent, the combined aqueous phase was extracted with methylene chloride (CH$_2$Cl$_2$) (3×4 L). The CH$_2$Cl$_2$ layers were combined and evaporated to dryness to afford extract AE (42 g). The remaining acqueous phase was centralized and adjusted to PH=12 with 5 N sodium hydroxide (NaOH) solution, and then extracted with CH$_2$Cl$_2$ (3×3 L) to afford an extract BE (10 g). The partial extract AE (25 g) was absorbed and chromatographed on a Diaion HP-20MG column (ID 8 cm, 60 cm deep) and eluted with 10% MeOH in water, 40% MeOH in water plus 0.5% AcOH, MeOH, and acetone to yield fractions A1, A2, A3, and A4, respectively. After development of TLC plate (silica gel) in BuOH:AcOH:H$_2$O (BAW, 5:1:4) solvent system, the plate was dipped into the Dragendorff's reagent and found that the alkaloid-positive spots were in fraction A2. A2 was subfractioned over normal phase silica gel column chromotagraphy using as solvent system CH$_2$Cl$_2$:MeOH:AcOH (20:1:0.1–9:1:0.1) mixtures to give 7 combined fractions B1–B7. Subfraction A5 was fractionated over a Al$_2$O$_3$ (acid type) column eluted with CH$_2$Cl$_2$:MeOH:H$_2$O (20:1:0.1–9:1:0.1) mixtures to yield a crude alkaloid fraction which was further purified by a combination of column chromatography and preparative HPLC on silica gel to yield compound 1 (310 mg) and 2 (180 mg). Both compounds 1 and 2 were well crystallized to afford white needles in acetone and white plates in 10% acetone/MeOH.

Macaline A (1). White needles from acetone; mp 128–30° C.; UV (MeOH) λ$_{max}$: 213, 229 (nm); IR (film) ν$_{max}$ 1641

(C=CH$_2$), 1265, 1167 cm$^{-1}$; $^1$H and $^{13}$C NMR (CDCl$_3$), see Table 1; (+)-ESIMS m/z 277 [M-Cl]$^+$, 186 [M-Cl-methylenebenzyl]$^+$, 91 [methylenebenzyl]$^+$. HRFABMS: calcd for C$_{19}$H$_{21}$N$_2$ 277.1704, found 277.1717.

Macaline B (2). White plates from acetone, mp 143–5° C.; UV (MeOH) $\lambda_{max}$: 213, 229 (nm); IR (film) $v_{max}$ 1640 (C=CH$_2$), 1263, 1169 cm$^{-1}$; $^1$H and $^{13}$C NMR (CDCl$_3$), see Table 1; (+)-ESIMS m/z 291 [M-Cl]$^+$, 200 [M-Cl-methylenebenzyl]$^+$, 91 [methylenebenzyl]$^+$.

X-ray Experimental Data and Structure Analysis of 1: Crystal Data. C$_{19}$H$_{21}$N$_2$Cl, M$_r$=312.846, Monoclonic, C2/c, a=18.799(4), b=10.101(2), c=9.612(2) Å, β=111.11(2)°, V=1702.7(6) Å$^3$, Z=4, D$_c$=1.22 g cm$^{-3}$, $\mu$(Mo-Kα)=2.203 cm$^{-1}$, Data Collection and Processing. The size of the crystal used for data collection was approximately 0.24×0.36×0.88 mm. The structure was solved by a multiple-solution procedure and was refined by full-matrix least squares. In the final refinement, the nonhydrogen atoms were refined anisotropically. The hydrogen atoms were included in the structure-factor calculations, but their parameters were not refined. The final discrepancy indices are R=0.049, Rw=0.049 for the 850 observed reflections. The final difference map has no peaks greater than ±0.21eÅ$^{-3}$. Of the 1498 reflections for θ<25 (°), 850 were considered observed [I>3.0σ(I)].

The novel compound 1 was obtained as white needles in acetone, and its molecular formula of C$_{19}$H$_{19}$N$_2$ was determined by HRFABMS. The IR spectrum of 1 showed a strong aromatic absorbance at 1560 cm$^{-1}$. In $^{13}$C NMR spectrum of 1, only eight carbon signals were observed at δ 8.1 (q), 49.6 (t), 127.2 (s), 127.8 (d), 128.6 (d), 129.1 (d), 134.3 (s), and 135.5 (d), suggesting that the molecule of 1 is symmetrical to match the mass spectral data. Analysis of the $^1$H NMR signals at δ 5.41 (s), 7.31 (dd, J=8.8, 2.2 Hz), and 7.37–7.46 (m) and corresponding $^{13}$C NMR signals (gHMQC) at δ 49.6 (t), 127.8 (d), 128.6 (d), 129.1 (d), and 134.3 (s), indicated the appearance of a phenylmethylene group. This is supported by the COSY and gHMBC spectral data. A proton signal due to methyl group was observed as a singlet at δ 2.18, but the correlative carbon appeared in a very high field at δ 8.1 (q) in the gHMQC NMR experiment, similar to those of 1,3-di(4-fluorobenzyl)-4,5-dimethylimidazolium bromide, a synthesized product for the application as probes for intracellular pH determination. In the gHMBC NMR experiments of (1), the proton signal at 5.41 (s) exhibited other relevant cross-peaks at 127.2 (s) and 135.5 (d) attributable to C-2 and C-4 (5), respectively, apart from the ones of phenylmethylene moiety. On the other hand, H-2 showed two relevant cross-peaks at 49.6 (t) and 127.2 (s), assignable to the methylene group and C-4 (5), respectively.

The structure of this compound was confirmed by single-crystal X-ray diffraction analysis. In the crystal, (1) appears to be a chloride quaternary ammonium salt and the structure is symmetrical. A 2-fold symmetry axis passes through C-2, its hydrogen, and the chloride ion. The bond distances N1—C2 1.325 Å, N1—C5 1.393 Å, and the carbon-carbon double bond 1.342 Å in the imidazole ring indicate that there is little delocalization in this ring. A perspective drawing of a molecule of MACA-N is shown in the FIG. 1. Assignments of all protons and carbons of 1 (Table I) were made by performing appropriate $^1$H—$^1$H COSY, DEPT, gHMQC, and gHMBC NMR experiments. Table 1. $^1$H and $^{13}$C NMR Spectral Data of Compounds 1 and 2 in DMSO-d$_6$ (400 MHz, δ in ppm).

TABLE 1

| Position | 1 | | 2 | |
|---|---|---|---|---|
| | $^1$H | $^{13}$C | $^1$H | $^{13}$C |
| 2 | 9.04 (s) | 135.5 d | | 145.1 s |
| 2-Me | | | 2.61 s | 10.6 q |
| 4,5 | | 127.2 s | | 128.0 s |
| 4,5-Me | 2.18 (s) | 8.1 q | 2.23 (s) | 8.7 q |
| 1' | | 134.3 s | | 135.3 s |
| 2',6' | 7.31 dd (8.8, 2.2) | 127.8 d | 7.14 dd (8.8, 2.2) | 127.4 d |
| 3',5' | 7.37–7.46 m | 129.1 d | 7.36–7.44 m | 130.5 d |
| 4' | | 128.6 d | | 129.6 d |
| —CH$_2$— | 5.41 s | 49.6 † | 5.46 s | 49.5 † |

J values (Hz) in parentheses.

Compound 2, white plates, showed a molecular ion peak at m/z 291, 14 amu higher than that of 1 in its low-resolution ESIMS. The $^1$H and $^{13}$C NMR spectra (Table 1) of 2 exhibited similar signals as present in 1, but with the absence of H-2 signal. Analysis of the $^1$H and $^{13}$C NMR spectra of 2 indicated that there was an methyl group at C-2 position of the imidazole ring, from the observation of signals at δ 2.61 (3H, s) and 10.6 (q), respectively. This inference as also supported by gHMQC and gHMBC NMR experiments. In a gHMBC MR experiment performed on 2, the proton signal showed one relevant cross-peak with the carbon signal at δ 145.1 (s), attributable to C-2. Thus, the structure of 2 was established as 1,3-dibenzyl-2,4,5-trimethylimidazolium chloride, namely lepidiline B.

To determine the cytotoxicity of compounds (1) and (2), screening assays were performed; these activities are summarized in Table 2 (set out below).

TABLE 2

Cytotoxic Activity of Isolates Obtained from L. meyenii.[a]

| Compound | Cell line[b] | | | | | | | |
|---|---|---|---|---|---|---|---|---|
| | A-549 | UMUC3 | HT-29 | PC-3 | PACA2 | A498$_2$LM | MDA231 | FDIGROV |
| 1 | >10 | >10 | >10 | >10 | >10 | >10 | >10 | 7.39 |
| 2 | >10 | 6.47 | >10 | >10 | 1.38 | >10 | 1.66 | 5.26 |

[a]Results are expressed as ED$_{50}$ values (μg/mL).
[b]Key: A495 = human lung carcinoma; UMUC3 = human bladder carcinoma; HT-29 = human colon adenocarcinoma; PC3 = human prostate adenocarcinoma; PACA2 = human pancreatic adenocarcinoma; A498$_2$LM = human kidney carcinoma; MDA231 = human breast carcinoma; FDIGROV = human ovarian carcinoma.

Compounds (1) and (2) were evaluated against a panel of human cancer cell lines as summarized in Table 2. Compound (1) was found to be weakly active only against the FDIGROV cell line (ED50 7.39 mg/ml). Compound (2) showed the cytotoxic activity against the UMUC3, PACA2, MDA231, and FDIGROV cells lines with ED50 values of 6.47, 1.38, 1.66, and 5.26 mg/ml, respectively. Compounds (1) and (2) were inactive against the A-549, HT-29, PC-3, and A4982LM cell lines.

The foregoing description is considered as illustrative only of the principles of the invention. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. Furthermore, since a number of modifications and changes will readily occur to those skilled in the art, it is not desired to limit the invention to the exact construction and process shown described above. Accordingly, all suitable modifications and equivalents may be resorted to falling within the scope of the invention as defined by the claims which follow.

The embodiments of the invention in which an exclusive property or privilege is claimed are defined as follows:

1. A method of treating ovarian carcinoma in a patient which comprises administering to said patient a compound of the formula:

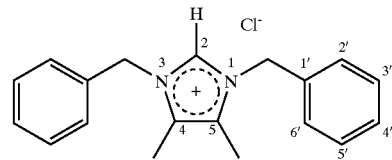

wherein R is H or Me.

2. A method of treating a proliferative disease, which comprises administering to a patient suffering from said proliferative disease a compound of the formula:

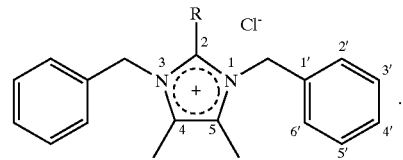

wherein R is H or Me and said proliferative disease is bladder carcinoma, pancreatic adenocarcinoma, breast carcinoma, or ovarian carcinoma.

* * * * *